United States Patent [19]

Wintersdorff

[11] 4,269,974

[45] May 26, 1981

[54] CLABBER-FREE XANTHAN GUM

[75] Inventor: Peter Wintersdorff, San Diego, Calif.

[73] Assignee: Merck & Co., Inc., Rahway, N.J.

[21] Appl. No.: 93,961

[22] Filed: Nov. 14, 1979

[51] Int. Cl.$^3$ .................................................. C08B 37/00
[52] U.S. Cl. .................................... 536/114; 426/589
[58] Field of Search ........................................ 536/114

[56] References Cited

U.S. PATENT DOCUMENTS

| | | | |
|---|---|---|---|
| 3,415,927 | 12/1968 | Butensky et al. | 536/114 |
| 3,729,460 | 4/1973 | Patton | 536/114 |
| 4,074,043 | 2/1978 | Jones et al. | 536/114 |

Primary Examiner—Johnnie R. Brown
Attorney, Agent, or Firm—Gabriel Lopez; Hesna J. Pfeiffer; Julian S. Levitt

[57] ABSTRACT

A novel form of xanthan gum and preparation therefor are disclosed. This gum is characterized in that when homogenized with oil and water, the resulting emulsion is smooth flowing (clabber-free).

5 Claims, No Drawings

CLABBER-FREE XANTHAN GUM

BACKGROUND OF THE INVENTION

Oil-in-water emulsions stabilized with xanthan gum are known to become semi-gelled or "clabbered" upon exposure to the high shearing action produced by colloid mills or homogenizers used in commercial processes. The chunky-flow property of the sheared emulsion is particularly undesirable in, e.g., salad dressings and in other systems which require high shear processes for optimum product features, such as ice cream, sauces, and gravies. A dressing containing medium (15–35%) to high (35–80%) oil levels can be smoothed out by subsequent stirring of the dressing or by the pumping action of the bottling stage. Unfortunately, the objectionable clabber is permanently retained in low oil dressings, i.e., those with less than 15% oil. It is now found that sufficient shearing of xanthan gum beer (i.e., fermentation broth) either diluted or undiluted prior to subsequent work-up in the production of xanthan gum eliminates the clabber phenomenon. Hence, low oil level salad dressings containing the rehydrated xanthan gum made from sheared beer can be colloid milled or homogenized without developing a clabbered texture.

SUMMARY OF THE INVENTION

A novel form of xanthan gum is disclosed, characterized in that it forms a smooth-flowing or clabber-free emulsion when homogenized with oil and water. The method of preparation of this form of xanthan gum is also described.

DESCRIPTION OF THE INVENTION

Xanthan gum, as used herein, refers to the biosynthetic polysaccharide produced by the organism *Xanthomonas campestris* by the whole culture fermentation of a medium comprising a fermentable carbohydrate, a nitrogen source, and appropriate other nutrients, said gum having a calcium ion concentration of about 1000 to about 2200 ppm.

Xanthan gum preparation is described in numerous publications and patents, e.g., U.S. Pat. Nos.
3,671,398
3,433,708
3,271,267
3,594,280
3,427,226
3,251,749
3,591,578
3,391,061
3,020,206
3,481,889
3,391,060.

The production of xanthan gum beer, the starting material in the practice of the present invention, by *Xanthomonas campestris*, NRRL B-1459, under a variety of fermentation conditions is well known. An inventive feature of this application relates to the shearing of said beer after fermentation is complete, a process which is independent of the biosynthetic pathway of the Xanthomonas organism in its production of the beer. It would be apparent therefore to one skilled in the art that the invention is operative using either B-1459 or a proprietary mutant strain of *Xanthomonas campestris* known by applicant's assignee to produce xanthan gum is somewhat higher yields than does B-1459. Since the function of the microorganism is merely to produce said xanthan gum beer, availability of this mutant strain is not significant to the practice of this invention.

Xanthan gum capable of producing smooth flowing emulsions is useful where chunky flow characteristics are undesirable, for example, in salad dressings, pharmaceutical antacid suspensions, chocolate syrups, sauces, gravies, or any emulsion or suspension which requires high shear in the preparation thereof.

Another use of the gum of this invention is in enhancing the stability of oil-water emulsions formed by the addition of surfactants to brine-oil mixtures. This technique relates in general to the recovery of oil from subterranean oil reservoirs by injection and flooding with surface-active agents and thickened aqueous systems.

Miscible recoveries are normally effected by displacement techniques where a fluid or fluids which are miscible with the reservoir oil are injected into a reservoir and serve to displace the oil from the pores of the reservoir driving it to the production well.

It is known that xanthan gum solubilized in aqueous systems imparts a viscosity increase. Polymer floods have been utilized for some time as a method of secondary and tertiary oil recovery. In addition, thickened polymer floods are also used as mobility controlling agents in surfactant flooding.

Increased oil recovery through the use of surfactants is known in the oil industry. Commonly an oil-water emulsion containing surface active agents is injected into the reservoir. The surfactants reduce the interfacial tension between the oil and the water, lowering the retentive capillary forces and increasing displacement efficiency.

It is thus seen that crude oil recovery is the most efficient when the emulsion containing the surfactant maintains its integrity through the displacement process.

The reservoir oil can be recovered from a formation through a production well by injecting into the formation through an injection well an oil-water emulsion stabilized by the addition of a quantity of clabber-free xanthan gum experimentally found to promote integrity of the mixture. This stabilized emulsion slug is subsequently driven through the formation by an aqueous driving fluid.

A representative oil-water emulsion for such use would be prepared from 0.2 wt. fraction oil, 0.79 wt. fraction water and 0.01 wt. fraction of a petroleum sulfonate. This emulsion is stabilized with about 500 ppm clabber-free xanthan gum.

It is known by those skilled in the art that "shear" is applied to xanthan gum at many different times either in its manufacture or during its utilization. Xanthan gum beer has to be constantly sheared during fermentation so that the Xanthomonas organism can grow. Xanthan gum powder must be sheared in order to hydrate it. Aqueous gum solution such as salad dressings are sheared during standard commercial processes. However, none of this "shear" is sufficient to produce the clabber-free product of the present invention.

On the other hand, from the following description it will be apparent to those skilled in the art that many different methods of shearing the beer can be utilized so as to obtain a clabber-free product. All of these come within the scope of this invention. The preferred mode, because of speed and practicality, is the use of a homogenizer or shear plate assembly.

In order to produce clabber-free xanthan gum, the type and length of shear is important. Shearing devices such as the Waukesha Shear Pump (Waukesha Foundry Co., Inc., Waukesha, Wisconsin), Homo-Mixer, (Gifford Wood Co., Hudson, N.Y.) and Cowles Impeller mounted on a Powermatic drill press Model 1150, require too much shearing time to be economically feasible. Four passes through either of two turbine devices (De Flaker Model EO, Morden Machine Co., Portland, Oregon, and the Vibroreactor Micromixer, Cherry-Barrel Corp.) produced no noticeable shearing. Neither did 45 minutes with the Hydrapulper (Black Clawson Co.). The Cowles Dissolver (Morehouse Cowles) and the RP-6K115 Disintegrator (Reitz Manufacturing Co.) produced favorable results. However, homogenizers and similar devices (e.g., shear plate assemblies) have been found to be the best shearing devices. One or two passes of xanthan gum beer through a homogenizer at high pressure provide the necessary shear for obtaining clabber-free xanthan gum in the shortest possible time. Shear plate assemblies (i.e., tubes containing equidistantly spaced circular plates, each having a small orifice) require slightly longer shear tme. Other high pressure devices could be engineered to economically produce clabber-free xanthan gum.

Volume; temperature; container configuration, and blade size, shape, speed, and sharpness can all be factors in preparing clabber-free xanthan gum. For example, a 500 ml solution of xanthan gum and water (1:1) can be sheared in a common Kitchen Waring Blender or Osterizer set at its highest speed for five minutes to produce the clabber-free product. A similar solution sheared by a dull-edged, 3-bladed propeller can be sheared for up to one hour without changing the rheological properties of the resultant xanthan gum. If a larger volume of solution is placed into a gallon sized Waring blender much longer shearing time is required to produce the clabber-free product.

It has also been found that the rheological properties of xanthan gum are permanently changed by high shear (or a combination of high heat and high shear). After the treatment, the xanthan gum solution has the following unique rheological properties:

1. It is extremely heat stable upon further high-heat exposures. The product is almost completely heat stable under food processing conditions such as HTST (high temperature, short time) or canning.

2. It exhibits an excellent reversible heat-thinning property, especially in the presence of salts at high temperatures (121° C. or higher).

Shear-treated (or heat and shear-treated) xanthan gum is of particular significance in canning or other processes requiring a heat-stable thickener with a reversible heat-thinning property.

The following examples are included to show the effects of different parameters on clabber-freeness and are not to be construed as limitations.

All temperatures are in degrees Celcius.

EXAMPLE 1

Homogenizer Shearing Method

One to three liter samples of undiluted, pasteurized xanthan gum beer were passed through a Manton-Gaulin homogenizer Model 15M. Two passes through the homogenizer at 7500 psi (6000 psi, 1st stage; 1500 psi, 2nd stage) were necessary to obtain a clabber-free product. The influence of temperature was significant, but far less critical than that of pressure, e.g., beer sheared once at 7500 psi at 93° C. produced considerably less clabber than beer sheared once at room temperature. The results of various combinations of temperature and pressure are tabulated below.

| Passes | PSI 1st stage | PSI 2nd stage | Temp (°C.) | Clabber |
|---|---|---|---|---|
| 2 | 6000 | 1500 | R.T. | none |
| 2 | 6000 | 1500 | 76.7° | none |
| 2 | 6000 | 1500 | R.T. | none |
| 1 | 6000 | 1500 | R.T. | light |
| 1 | 6000 | 1500 | 93.3° | trace |
| 2 | 6000 | — | 76.7° | trace |
| 2 | 6000 | — | 93.3° | trace |
| 2 | 5000 | — | 76.7° | light |
| 1 | 5000 | — | 76.7° | heavy |
| 1 | 8500 | 1500 | 76.7° | trace |

EXAMPLE 2

Shear Plate Assembly

A shear plate assembly, which utilizes the homogenizer principle, was used. It consists of a length of a 3-foot long X 1-inch diameter pipe in which are three equally spaced metal plates with a 1/16" hole through the center of each plate. Approximately 500 ml of beer was pumped under high pressure through the pipe at room temperature, creating a pressure drop across the first plate of 500-700 psi. The results are tabulated below.

| Passes | Clabber | Beer Visc. (cP) |
|---|---|---|
| 0 | heavy | 4350 |
| 1 | heavy | 4950 |
| 2 | heavy | 4700 |
| 3 | medium | 4650 |
| 4 | slight | 4750 |
| 5 | none | 4650 |

Beer pushed five times through a one-plate shear plate assembly produced near clabber-free xanthan gum.

When five plates were used in the pipe, and the pressure drop across the first plate was raised to about 1700 psi, five passes were necessary to produce clabber-free xanthan gum.

EXAMPLE 3

Homo-Mixer

The mixer utilizes a high speed turbine mechanism. The turbine action forces materials through restricted openings in a stator where they are subjected to the intense forces of impact and hydraulic shear. One gallon of beer at 4.4° C. was sheared for 45 minutes at 7200 rpm using a 1.7" shear head. Temperature rose to 51.7° C. Very slight clabber was observed in a low-oil emulsion made from this sheared beer.

EXAMPLE 4

Cowles Impeller

The shearing device consists of a 3" Cowles Impeller (B1503) attached to the end of a shaft, mounted on a Powermatic drillpress Model 1150. The rotating impeller causes hydraulic attrition, which is a combination of violent impact and shearing of particle against particle. 15 minutes at 4800 RPM (maximum speed) was required for effective shear for a 500 gm sample of beer.

EXAMPLE 5

Manton-Gaulin Colloid Mill

A nearly clabber-free product was obtained with 15 passes of xanthan gum beer through a Manton-Gaulin Colloid Mill set at 0.005" clearance.

EXAMPLE 6

Cowles Dissolver

A laboratory Cowles Dissolver supplied with a standard 4-inch blade and an extended blade with flat cutting edges giving a 4½inch diameter was used. Effective shear was obtained in 10 minutes on a 1500 ml sample of beer at a speed of 5900 RPM.

EXAMPLE 7

RP-6K115 Disintegrator

This unit utilizes an enclosed stack of flat knives turning at 12000 RPM. The enclosure maximizes knife-beer contact. Three passes at one gpm feed were required for proper shear. The enclosure for the knives may consist of a screen, perforated plate, or solid plate with a discharge opening. The only effective enclosure was the solid plate with the discharge opening at the 12:00 o'clock position.

EXAMPLE 8

Clabber-Free Tests

One test for determining when the shearing is complete (i.e., when clabber-free xanthan gum has been produced) is as follows:

The xanthan gum is precipitated from the sheared beer, preferably with isopropanol (IPA). An IPA/beer ratio of 1:1 is recommended for this test. The mixture is filtered and the residual IPA is pressed out. The xanthan gum fibers are dried in a steam oven at 50° C. for 5 hours and then milled to a powder. A slurry of 6.4 g of this powder in 40 g of vegetable oil is added to 500 ml H$_2$O with stirring. After hydration (for example, about 0.5 hr. on a Lightnin mixer, or equivalent) 26 g of NaCl and 75 ml of 10% acetic acid are added. The emulsion is milled on a Manton Gaulin colloid mill at a setting of 0.015". If the milled emulsion has smooth flow properties, shearing was complete and clabber-free xanthan gum was produced.

Another test is as follows:

Two samples (KTL1 and KTL2) of pasteurized xanthan gum fermentation beer were sheared as described in Example 1 (room temperature, 6000 psi 1st stage, 1500 psi 2nd stage, 2 passes). Both samples were precipitated with IPA and stream dried at 50° for 5 hours. KTL1 was milled through an 80-mesh screen; KTL2 through a 20-mesh screen. Unsheared controls (i.e., prepared according to the normal commercial process without the additional shearing step) were similarly precipitated and milled. Milled emulsions consisting essentially of 6.4 g (1.0%) gum, 40 g (6.0%) vegetable oil, 500 ml (80%) H$_2$O, 75 g (12%) 10% acetic acid and either 0% or 1% KCl.

Viscosity profiles at low shear rates were determined using the spring relaxation method on the Wells-Brookfield plate and cone viscometer. Working yield values (shear stress at a shear rate of 0.01 sec$^{-1}$) were determined at room temperature and the results tabulated below. Working yield value in an extrapolation of a viscosity curves to near-zero shear rates obtained from shear rate vs. shear stress plots.

| Sample | % Solids | Working Yield Values* | |
|---|---|---|---|
| | | 0% KCl | 1% KCl |
| Control for KTL1 | 92 | 37 | 50 |
| KTL1 | 92.8 | 25 | 25 |
| Control for KTL2 | 96.7 | 27 | 63 |
| KTL2 | 93.3 | 21 | 29 |

*dynes/cm$^2$

The clabber-free KTL$_1$ in a 1% KCl emulsion showed a 50% reduction in working yield value compared to its control; KTL2 showed a 54% reduction. In salt-free emulsions the respective differences are 33% and 22%.

This constitutes a more accurate test for clabber-freeness, i.e., shearing of the beer is complete when a 1% KCl emulsion, as described above, reduces the working yield value at a shear rate of 0.01 sec$^{-1}$ by at least 50%.

EXAMPLE 9

Low Calorie French Dressing

The clabber-free property of this novel form of xanthan gum makes it useful in several applications. For example, gum concentrations of 1-2% are common in low calorie (low oil content) dressing. The high degree of pseudoplasticity of xanthan gum would be very functional in eliminating gumminess in low calorie dressings except for its tendency to clabber when subjected to the shear produced during the standard milling process. Eliminating this clabber effect of xanthan gum by the shear method of this invention has enabled formulation of low calorie dressings having exceptional texture and mouthfeel. Dressing containing 0.5-1.2% clabber-free xanthan gum and about 6% vegetable oil are preferred.

The formulation listed below is a low calorie French dressing having over 1 year emulsion stability at room temperature. Values given are in % (wt/wt).

| | | |
|---|---|---|
| Xanthan Gum (clabber-free) | | 0.5-1.0% |
| Vegetable Oil | | 0.1-15% |
| Vinegar - 50 grain | | 12-18% |
| Salt | | 1.5-3.5% |
| Tomato paste | | 5-10% |
| Mustard flour | | |
| Paprika | spice mix | 0.75-1.5% |
| Onion powder | | |
| Garlic powder | | |
| Egg yolk | | 1-3% |
| Water | | 49-65% |
| Sweetner (to taste) | | 0.05-0.10% |

Procedure:
(1) Slurry xanthan gum in the vegetable oil and add to the water with agitation.
(2) After hydration, add tomato paste, and vinegar.
(3) Add egg yolk and all remaining solids.
(4) Stir emulsion until uniform and then colloid mill at 0.015".

The following is a preferred formulation:

| | |
|---|---|
| Xanthan gum (clabber-free) | 0.75% |
| Vegetable Oil | 6.00% |
| Vinegar-50 grain | 18.00% |
| Salt | 3.50% |
| Tomato paste | 7.50% |
| Mustard flour | 0.50% |

-continued

| | |
|---|---|
| Paprika | 0.60% |
| Onion powder | 0.10% |
| Garlic powder | 0.05% |
| Egg yolk | 2.00% |
| Water | 55.75% |
| Sweetner (to taste) | 0.05-0.10% |

EXAMPLE 10

Viscosity Increase

Xanthan gum is prepared from beer which is recirculated through a colloid mill at 0.001" clearance. A French dressing is prepared using this gum compared to a dressing made from xanthan gum prepared from unsheared beer. The following viscosity data are obtained which show the slight increase in viscosity obtained from sheared gum.

| % Gum | Visc. (cP) |
|---|---|
| 0.20% from sheared beer | Initial = 2010 |
| | After milling = 2900 |
| | After 24 hrs. = 3600 |
| 0.20% from unsheared beer | After 24 hrs. = 34-3500 |

EXAMPLE 11

Effect of Enzyme Addition

A sample of xanthan gum beer is diluted with deionized water 1:1. After 15 passes through a colloid mill (0.020"), the solution is treated with 1000 ppm Maxatase. (Alternatively, the enzyme can be added prior to colloid milling.) This mixture is put on a Sunbeam blender at 25% power for 5 minutes to disperse the enzyme. The resulting mixture is incubated at 38° C. for 3 hours. After precipitation in IPA, the fiber is washed, dried, and milled (40 mesh). The resulting snowy white product has improved dispersing characteristics. Clarity of the resulting dilute solutions of polymer in both deionized water and in brine is improved and is attributed to the addition of the enzyme after shearing. Viscosity is measured at 1000, and 500 ppm in both deionized water and standard brine. For comparison, a brine solution is prepared from xanthan gum that is precipitated from beer which has been neither sheared nor enzyme treated. The following data are obtained.

| | Visc. (cP) |
|---|---|
| Treated gum (D.I. water) | |
| 1000 ppm | 67.8 |
| 500 ppm | 29.2 |
| Treated Gum | |
| (Standard brine) | |
| (10,000 ppm $Na^+$, 1000 ppm $Ca^{++}$) | |
| 1000 ppm | 46.6 |
| 500 ppm | 16.1 |
| 250 ppm | 6.6 |
| Control Gum (Standard brine) | |
| 1000 ppm | 19.4 |

The gum prepared as by this example is particularly useful in drilling, workover, and completion fluids for oil and gas wells. For comparison two fluids are prepared containing 0.28 % by weight xanthan gum (one gum prepared as in this example, the other commercially available xanthan gum, i.e., not shear or enzyme treated), 15.7% by weight Glen Rose Shale, and 1.4% by weight bentonite in tap water. At high shear rates, about 500 $sec^{-1}$, the viscosities of both fluids are comparable (80 cP vs. 90 cP). However, at low shear rates, 5 $sec^{-1}$, the viscosities differ significantly (about 240 cP for the untreated gum vs. about 450 cP for the treated). This indicates that the treated gum is more pseudoplastic and would improve the hole cleaning and barite suspension properties of drilling fluids.

What is claimed is:

1. Clabber-free xanthan gum, wherein a milled emulsion consisting essentially of 1.0% said gum, 6.0% vegetable oil, 80% $H_2O$, 12% acetic acid (10%), and 1% KCl exhibits at room temperature a working yield value at a shear stress of 0.01 $sec^{-1}$ at least 50% less than a control emulsion consisting essentially of 1.0% unsheared xanthan gum, 6.0% vegetable oil, 80% $H_2O$, 12% acetic acid (10%), and 1% KCl.

2. Clabber-free xanthan gum wherein a milled emulsion consisting essentially of 1.0% said gum, 6.0% vegetable oil, 77% $H_2O$, 3% NaCl, and 13% acetic acid (10%) exhibits smooth flow properties.

3. A process for producing clabber-free xanthan gum which comprises shearing pasteurized xanthan gum beer.

4. The process of claim 3 where the shearing is comparable to that produced by passing the undiluted beer at room temperature twice through a Manton-Gaulin Model 15M homogenizer at 7500 psi.

5. The process of claim 4 which comprises the further step of precipitating the clabber-free xanthan gum with isopropanol.

* * * * *